United States Patent [19]
Rubens et al.

[11] Patent Number: 5,609,631
[45] Date of Patent: Mar. 11, 1997

[54] FIBRIN D-DOMAIN MULTIMER COATED PROSTHESES AND METHODS FOR THEIR PRODUCTION

[76] Inventors: Fraser D. Rubens, 27 Castlethorpe Cresc., Nepean, Ontario, Canada, K2G 5P9; Paul D. Bishop, 28425 SE. 8th St., Fall City, Wash. 98024

[21] Appl. No.: 430,792

[22] Filed: Apr. 28, 1995

[51] Int. Cl.$^6$ .............................. A61F 2/02; A61K 37/547
[52] U.S. Cl. .................. 623/11; 435/180; 424/94.64; 427/2.24; 427/2.25; 427/2.26; 427/2.28; 427/2.3; 427/2.31; 600/36
[58] Field of Search .................................. 600/36; 623/1, 623/11, 12; 128/898; 424/94.64; 427/2; 435/1, 180

[56] References Cited

U.S. PATENT DOCUMENTS

| | | | |
|---|---|---|---|
| 5,204,447 | 4/1993 | Bishop et al. | 530/381 |
| 5,230,693 | 7/1993 | Williams . | |
| 5,272,074 | 12/1993 | Rubens | 435/180 |
| 5,324,647 | 6/1994 | Rubens et al. . | |

FOREIGN PATENT DOCUMENTS 0366564 of 1989 European Pat. Off. .

OTHER PUBLICATIONS

"Precoating Expanded Polytetrafluoroethylene Grafts Alters Production of Endothelial Cell–Derived Thrombomodulators", *Journal of Vascular Surgery*, Li et al. pp. 1010–1017 (1991).

"Inhibition of Thrombus Formation In Vivo By Novem Antiplatelet Agent", Marzec et al., pp. 367–371 Artieriosclerosis, (1989).

"The Effect of Antithrombin III–Independent Thrombin Inhibitors and Heparin on Fibrin Accretion Onto Fibrin-Coated Pollyethylene", Rubens et al., *Thrombosis and Haemostasis*, pp. 130–134 (1993).

"Implantation of In Vitro Endothelialized Polytetrafluoroethylene Grafts In Human Beings", Kadletz, et al., pp. 736–742, *Journal of Thoracic and Cardiovascular Surgery* (1992).

"Endothelial Cell Seeding: Coating Dacron and Expanded Polytetrafluororthylene Vascular Grafts With A Biological Glue Allows Adhesion and Growth of Human Saphenous Vein Endothelial Cells", Mazzucotelli et al., pp. 482–490, *The International Journal of Artificial Organs*, (1991).

"In Vitro Endoothelialization of Small–Caiiber Vascular Grafts", Anderson et al., pp. 577–586, *Surgery*, (1987).

"Endothelial Cell Seeding of Polytetrafluoroethylene Vascular Grafts in Humans: A Preliminary Report", Zilla, et al., pp. 535–541, *Journal of Vascular Surgery* (1987).

"Allogenic, Multidonor In Vitro Endothelialization of Small Diameter PTFE Grafts in Baboons", Fasol, et al., pp. 64–71, *Vascular Surgery* (1991).

"Thermal Desorption Spectrometry of Fibrinogen", Voegel et al., pp. 134–144, *Colloieds and Surfaces* (1987).

"Precoating Substrate and Surface Configuration Determine Adherence and Spreading of Seeded Endothelial Cells on Polytetrafluoroethylene Grafts", Kaehler et al., pp. 535–541, *Journal of Vascular Surgery* (1989).

"Immobilization of Soluble Fibrin on Factor XIIIa–Coated Polystyrene Beads Mediated by N–Terminal Fibronectin Fragments", Hormann, et al., pp. 427–430, *Biol. Chem. Hoppe–Seyler* (1991).

"Bioartificial Polymeric Materials Obtained from Blends of Synthetic Polymers With Fibrin and Collagen", Soldani et al., pp. 295–303, *The International Journal of Artificial Organs* (1991).

"Endothelial Cell Seeding Efficiency Onto Expanded Polytetrafluorethylene Grafts With Different Coatings", Lindblad et al., *Acta Chir Scand* 152, (1986).

"New Biolized Pollymers For Cardiovascular Applications", Giusti et al., pp. 476–480.

"Platelet Aggregation by Fibrinogen Polymers Crosslinked Across the E Domain", McManama et al., pp. 363–371, *Blood* (1986).

"Fibrin Degradation Product D–Dimer Induces The Synthesis and Release of Biologically Active IL–1β IL–6 and Plasminogen Activator Inhibitors From Monocytes In Vitro", Robson et al., pp. 322–326, *British Journal of Haematology*, (1994).

"The Effect of Preclotting and Collagen Coating on Endothelializing Rate and Thrombogenesity of Dacron Grafts in the Canine Thoracic Aorta", Niibori, et al., p. 515, *The Journal of the Japanese Association for Thoracic Surgery* (1994).

"Prelining of Polytetrafluoroethylene Grafts With Cultured Human Endothelial Cells Isolated From Varicose Veins", Leseche et al., pp. 36–45, *Surgery* (1989).

"Platelet Interactions With the Vessel Wall and Prosthetic Grafts", Rubin et al., pp. 200–207, *Basic Science* (1993).

*Primary Examiner*—John G. Weiss
*Assistant Examiner*—Francis K. Cuddihy

[57] ABSTRACT

Methods for coating a prosthetic surface with anti-thrombogenic, or anti-coagulant, proteins are disclosed. The methods involve contacting a surface of a prosthetic material with a composition containing multimers of fibrin degradation products. These multimers, preferably D-dimers, have cross-linked D-domains. The methods of the invention are useful for providing an anti-thrombogenic coating on prosthetic implants which are exposed to a patient's blood after implantation, for example vascular grafts and artificial heart valves.

20 Claims, No Drawings

FIBRIN D-DOMAIN MULTIMER COATED PROSTHESES AND METHODS FOR THEIR PRODUCTION

TECHNICAL FIELD

The invention relates to methods for coating prosthetic surfaces with anti-thrombogenic proteins, and to prosthetic devices prepared by those methods.

BACKGROUND OF THE INVENTION

A major limitation in developing prosthetic implants for medical use is that most prosthetic materials thus far developed tend to be excessively thrombogenic, i.e. they trigger excessive blood clot formation, or thrombosis, at surfaces of the implant exposed to the patient's blood. This problem can lead to severe complications, particularly in the case of prosthetic vascular grafts used to correct coronary artery disease, lower limb ischemia, arterial aneurysms and other circulatory problems. About 20% to 30% of patients undergoing vascular bypass or replacement surgery require prosthetic grafts, because autologous veins are unavailable due to previous surgery or other reasons. In these patients, there is a high rate of graft failure due to the high thrombogenicity of synthetic materials used to produce the prosthetic grafts. One multicenter study demonstrated that the cumulative 4-year patency of prosthetic grafts used for distal arterial reconstruction was only 12% for polytetrafluoroethylene (PTFE) grafts; far lower than the long-term patency observed for autologous grafts. Vieth et al. (*J. Vasc. Surg.* 3: 104–114, 1986).

The mechanism by which thrombosis occurs in prosthetic vascular grafts is generally well understood. Shortly after implantation of a synthetic graft, adsorption and accumulation of blood proteins on the lumenal surface of the graft begins. In particular, a surface coating of polymerized fibrin, referred to as the pseudointima, appears first, followed by an accumulation of thrombin bound to the fibrin. The thrombin contributes to platelet activation and formation of a platelet rich thrombus. Bound thrombin may also contribute to further fibrin accretion that in turn leads to distal embolism.

An important difference between prosthetic and autologous vascular grafts is that prosthetic grafts lack a lining of endothelial cells which cover the lumenal surface of natural vessels. It is widely believed that the endothelial lining provides an anti-thrombogenic effect and is among the most important factors in maintaining long term patency in autologous grafts. Accordingly, numerous attempts have been made to artificially seed endothelial cells onto surfaces of prosthetic grafts. (reviewed by Mosquera and Goldman, *Br. J. Surg.* 78: 656–660, 1991 ). Most of these efforts involved coating the prosthetic surface with a "biological glue," comprised of adhesive proteins and other materials which enhance endothelial cell adhesion and growth. These investigations have used a variety of extracellular matrix proteins and other materials, including fibrin, fibrin gels cross-linked with factor XIII, fibronectin, laminin, various forms of collagen, albumen and blood. Although endothelial seeding of grafts has shown beneficial results in experimental settings, the technology has not progressed sufficiently that seeded grafts suitable for routine use can be produced.

Another primary focus of research concerning prosthetic vascular grafts has involved efforts to develop non-cellular, anti-thrombogenic coatings, such as protein coatings, which may reduce the thrombogenicity of implanted grafts. One such study involved coating prosthetic surfaces with the anticoagulant protein heparin. Nagaoka et al. (*Artificial Organs* 17: 598–601, 1983). Other studies have used natural, extracellular matrix materials to coat vascular grafts. For example, European Patent No. 0 366 564 issued to Sawamoto et al. discloses polymeric materials coated with a hydrolyzed fibrin layer optionally cross-linked with factor XIII. In addition, U.S. Pat. No. 5,324,647 issued to Rubens et al. discloses polymeric materials coated with either a layer of fibrinogen, thermally denatured fibrinogen or factor XIII cross-linked fibrin. While various of these natural coatings are reported to have anti-thrombogenic effects, prosthetic materials treated with such methods have not yet been widely employed in a clinical setting.

In view of the above, there is a clear need in the art for prosthetic materials having improved biological compatibility over currently available materials. In particular, there is a need for prosthetic materials which have reduced thrombogenicity compared to available synthetic materials used for prostheses. Such materials should be resistant to the deposition of blood proteins and to platelet adherence. These materials would be useful for producing vascular grafts, synthetic heart valves, artificial organs and in any other application where a surface of the prosthetic material will be exposed to a patient's blood, so as to create a potential for thrombogenesis at the exposed prosthetic surface. The present invention provides such materials, as well as methods for preparing those materials. Materials prepared in accordance with the methods of the invention are useful for providing biocompatible implants, medical treatment methods employing such implants, as well as useful materials for experimental modeling of thrombogenic and fibrinolytic processes.

DISCLOSURE OF THE INVENTION

The present invention provides methods for coating prosthetic surfaces with anti-thrombogenic proteins, and prosthetic devices prepared according to those methods. The methods of the invention generally comprise contacting a prosthetic surface with a composition containing multimers of fibrin degradation products which have cross-linked D-domains, to produce an anti-thrombogenic coating of the multimers on the prosthetic surface. Fibrin degradation products useful within the invention are limited to fibrin degradation products possessing fibrin D-domains, preferably in the form of D-monomers or D-multimers generated by plasmin lysis. The multimers are also preferably formed by cross-linking the D-domains with Factor XIII, before or after the fibrin degradation products are generated.

It is preferred within the invention to contact the prosthetic surface with a composition that consists essentially of the multimers of fibrin degradation products in a suitable carrier. It is also preferred to use a liquid carrier to form a solution that is substantially free of intact fibrin, and of fibrin degradation products lacking D-domains.

In alternate embodiments of the invention, one or more additional agents are added to the composition of multimers to enhance endothelial cell growth on the anti-thrombogenic coating after the prosthetic surface has been contacted with the composition. Useful proteins for this purpose include a variety of extracellular matrix materials as well as chemotactic and/or cell growth factors. Specific agents contemplated for use in this manner include basic fibroblast growth factor, endothelial cell growth factor, β2 macroglobulin, vitronectin, fibronectin, and cell-binding fragments of fibronectin. In a related embodiment, coated prosthetic surfaces treated according to one of the above methods are seeded with endothelial cells to further enhance biocompatibility of the coated surface.

Within another aspect of the invention, the composition of multimers is a solution, and the prosthetic surface is incubated in the solution within a selected temperature range. Within one embodiment, the incubation is carried out between approximately 20° C. and 25° C. Within another embodiment, the incubation is conducted at a temperature sufficient to thermally denature the multimers, between about 56° C. and 100° C., preferably at about 70° C., in order to enhance adherence of the multimers onto the prosthetic surface.

Preferred prosthetic materials for use within the invention include a broad range of biologically compatible polymers known to have medically useful structures and prosthetic surface characteristics. Useful polymers within this context include polyethyleneterephthalate, polytetrafluoroethylene, expanded polytetrafluoroethylene, polymers of lactide-glycolide, polyglactin, polydioxanone, polyurethanes, polypropylenes and polyesters. Other useful materials with suitable prosthetic surfaces include stainless steel, titanium, cobalt chrome alloys and silicon-based materials.

Within another aspect of the invention, a variety of prosthetic devices are provided, which are made according to the coating methods of the invention. In alternate embodiments, the prosthetic surface to be coated is a surface of an artificial vascular implant, duct implant, heart valve, bone implant, patch or other artificial implant.

Within yet another aspect of the invention, methods of treating mammalian patients are provided which involve implanting into the patient a prosthetic member prepared by the above-disclosed methods.

These and other aspects of the invention will become apparent upon reference to the following detailed description.

DETAILED DESCRIPTION OF THE INVENTION

The present invention provides methods for coating prosthetic surfaces with anti-thrombogenic proteins, and also provides prosthetic devices prepared according to those methods. The methods of the invention generally comprise contacting a prosthetic surface with a composition containing multimers of fibrin degradation products which have cross-linked D-domains, to produce an anti-thrombogenic coating of the multimers on the prosthetic surface. As used herein, "anti-thrombogenic coating" refers to a surface layer, preferably a continuous surface coating, which confers a medically significant reduced thrombogenicity, or blood clot inducing effect, when the coated prosthetic surface is exposed to a platelet preparation, or to an actual patient's blood after implantation, compared to thrombogenicity of an uncoated surface. To determine a medically significant reduction in thrombogenicity, uncoated and coated prostheses are preferably implanted into a mammal for a sufficient period of time for adsorption and accumulation of blood proteins on a lumenal surface of the uncoated prosthetic surface. Subsequently, the uncoated and coated prostheses are removed and comparatively analyzed microscopically, or by other conventional methods, to determine whether the coating of multimers on the prosthetic surface confers an anti-thrombogenic effect, i.e. whether thrombus formation is significantly reduced due to the presence of the coating. Alternatively, several in vitro models may be used to determine the anti-thrombogenic effect of the multimer coating, for example models which compare protein adsorption and/or platelet adhesion on native fibrinogen coated surfaces to adsorption and/or adhesion on multimer coated surfaces.

A variety of fibrin degradation products are useful within the invention, but they are limited to degradation products which include substantially complete fibrin D-domains. As used herein, "D-domains" of fibrin generally refers to globular portions of the fibrin molecule disposed near opposite ends of the molecule. The D-domain includes roughly two-thirds of the carboxy termini of the fibrin β and γ chains, and a small portion of the carboxy terminus of the fibrin α chain (see *Hemostasis and Thrombosis, Basic Principals and Clinical Practice*, 3d edition, eds. R. W. Colman et al., J. B. Lippincott, Co., Philadelphia, 1994, herein incorporated by reference in its entirety; and see in particular Chapter 14, *Fibrinogen Structure and Physiology*, p. 277).

The fibrin degradation products useful in the invention are preferably D-monomers or D-multimers generated by plasmin lysis. Plasmin digestion of cross-linked fibrin in the presence of calcium gives rise to a series of cross-linked intermediate fragments including D dimers, trimers and tetramers, with D-dimers predominating (Siebenlist et al., *J. Biol. Chem.* 269: 28414–28419, 1994; Robson et al., *Brit. J. Haematol*, 86: 322–326, 1994, both herein incorporated by reference in their entirety). A suitable method for preparing D-domain from purified human fibrinogen is described in Delvos et al. (*Haemostasis* 18: 99–105, 1988), herein incorporated by reference in its entirety. Briefly, Fibrinogen is incubated with plasmin in the presence of $CaCl_2$ and, after the digestion has progressed an appropriate amount of time to yield the desired end products, the reaction is terminated by the addition of aprotinin. The digest is then passed over a Sepharose-lysine column, as described in Haverkate et al. (*Thromb. Res.* 10: 803–812, 1977). The effluent is then dialyzed against a sodium bicarbonate buffer and eluted from a DEAE-Sephadex column with a linear pH/salt gradient between the dialysis buffer and bicarbonate buffer. Samples from each protein-containing fraction are then assessed by SDS-PAGE. Fractions with the highest purity of D-domain are concentrated 10-fold by ultrafiltration. To prepare D-dimers, human fibrinogen is incubated in the presence of rFXIII, as described in Haverkate et al. (*Eur. J. Clin. Invest.* 9: 253–255, 1979). The cross-linked fibrin clot is squeezed with filter paper to remove entrapped liquid, frozen, lyophilized, ground to a fine powder, and resuspended (approx. 10 mg/mL) in an appropriate buffer containing plasmin. After plasmin digestion, aprotinin is added and the solution is chromatographed on Sepharose-lysine. D-dimer is isolated by passage of the effluent through a Sephacryl S-300 HR column. Fractions identified as containing D-dimer are then concentrated by ultrafiltration.

Although D-dimers are the preferred fibrin degradation products for use in the invention, other fibrin degradation products having substantially complete D-domains are also contemplated. Such alternate degradation products can be generated by a variety of conventional methods, such as limited trypsin digestion.

In a preferred embodiment of the invention, the prosthetic surface is contacted with a composition that consists essentially of the multimers of fibrin degradation products in a suitable carrier. A composition is defined as "consisting essentially of multimers of fibrin degradation products" if there are no additional substances present in the composition that materially alter the anti-thrombogenic effect of the multimer coating. It is also preferred to use a composition that is substantially free of intact fibrin, and of fibrin degradation products lacking D-domains. A solution is considered substantially free of intact fibrin and of fibrin degradation products lacking D-domains when it contains about 90% pure, multimeric fibrin degradation products that include D-domains. The composition which contains the multimers can be in the form of a liquid solution, a solid, such as a fine powder, a paste or a colloidal suspension. Suitable carriers include non-corrosive, biocompatible, solid or liquid carriers suitable for application to prosthetic materials, and in which the multimers remain intact and cross-linked.

Within a preferred embodiment of the invention, the composition of multimers is a solution, and the prosthetic surface is incubated in the solution within a selected temperature range. Preferred solutions include standard biological or medical buffers, such as low ionic strength aqueous buffers at near neutral pH, for example tris buffered saline (TBS). The incubation is carried out at a temperature at which the solution is a liquid and the prosthetic surface is not degraded. Within one embodiment of the invention, the incubation is carried out at less than 56° C., preferably less than 37° C., most preferably at about 20°–25° C., so that the multimers remain in an undenatured state. However, it may be preferable in certain applications to carry out the incubation at a temperature sufficient to thermally denature the multimers, between about 56° C. and 100° C., and preferably at about 70° C., to enhance adsorption of the multimers onto the prosthetic surface.

When a solution of multimers is used to coat the prosthetic surface, it is generally desired to provide a concentration of multimers in the solution of between about 0.05 mg/ml and 100 mg/ml. Preferably, the solution has a multimer concentration of between about 0.1 mg/ml and 10 mg/ml. Higher concentrations may be employed however, depending on solubility considerations, which may improve the rate or extent of adsorption of the multimers onto the prosthetic surface.

Preferred prosthetic materials for use within the invention include a broad range of biologically compatible polymers known to have generally useful structures and surface characteristics for medical or experimental, prosthetic purposes. Useful polymers within this context include polyethyleneterephthalate (eg. Dacron®), polytetrafluoroethylene, expanded polytetrafluoroethylene (eg. Gore-Tex®, W. L. Gore, Flagstaff, Ariz.), polymers of lactide-glycolide, polyglactin, polydioxanone, polyurethanes, polypropylenes and polyesters. Other useful materials with suitable prosthetic surfaces include stainless steel, titanium, cobalt chrome alloys and silicon-based materials.

The methods of the present invention are useful to produce a variety of prosthetic devices, such as artificial vascular implants, duct implants, urological implants, internal organs, heart valves, bone implants, patches, webs, or other artificial prosthetic structures, including those that are exposed to blood flow after implantation. More specifically, artificial duct implants which may be coated according to the methods of the invention include artificial urinary ducts, artificial kidney tubules, artificial lymphatic ducts, artificial bile ducts, artificial pancreatic ducts, indwelling catheters, shunts and drains. It is also contemplated that the methods of the invention may be effectively employed for imparting an anti-thrombogenic coating to heterograft or xenograft tissue or organ implants. Surfaces of such devices and implants are prepared as disclosed herein, and the devices or implants are implanted in a patient according to standard surgical techniques. In addition, the coated surfaces of the present invention provide a useful in vitro model for studying fibrin accretion, platelet adhesion and other phenomena related to vascular graft failure, as well as for testing of potential anti-thrombogenic agents.

Coated prosthetic surfaces prepared according to the present invention may be seeded with endothelial cells. Endothelial cell seeding of vascular grafts and other surfaces exposed to the blood provides prosthetic materials that are actively anti-thrombogenic and exhibit increased resistance to occlusion. The stability of the multimer coating makes it an excellent substrate for endothelial cell seeding. In alternate embodiments of the invention, one or more additional agents are added to the composition of multimers, to enhance endothelial cell growth on the prosthetic surface after it has been coated. Useful proteins for this purpose include a variety of extracellular matrix materials, as well as chemotactic and/or cell growth factors. Specific agents contemplated for use in this manner include basic fibroblast growth factor (basic FGF) and endothelial cell growth factor (vascular endothelial cell growth factor), $a_2$ macroglobulin, vitronectin, fibronectin, and fibronectin fragments containing binding determinants for endothelial cells. Preparation of these proteins and protein fragments is within the level of ordinary skill in the art. See, for example, Gospodarowicz et al., U.S. Pat. Nos. 4,785,079 and 4,902,782; Obara et al., *FEBS Lett.* 213: 261–264, 1987; Dufour et al., *EMBO J.* 2: 2661–2671, 1988; Tischer et al., WO 91/02058; Boel et al., *Biochemistry* 29:4081–4087, 1990; Ruoslahti et al., U.S. Pat. No. 4,614,517; Pierschbacher et al., U.S. Pat. No. 4,589,881; and Suzuki et al., *EMBO J.* 4: 2519–2524, 1985, which are incorporated herein by reference in their entirety. These proteins will generally be included in the multimer composition at concentrations between about 0.5 and 10 μg/mL.

Endothelial cells are obtained by standard procedures from umbilical vein, saphenous vein or other sources. See, for example, Balconi et al., *Med. Biol.* 64:231–245, 1986; Ryan et al., *Tissue Cell* 17: 171–176, 1985: Budd et al., *BR. J. Surg.* 76: 1259–1261, 1989. Cells can be harvested by mechanical or, preferably, enzymatic methods. Briefly, veins are flushed to remove blood and filled with a collagenase solution to dislodge the endothelial cells. The cells are collected and cultured in a conventional medium, generally at about 37° C. in a 5% $CO_2$ atmosphere. Satisfactory attachment of the cells to the coated prosthetic surface is generally obtained within one to two hours. In the alternative, cultured endothelial cells are added to the composition containing the multimers, thus trapping them within the coating. The coated prosthetic material is then incubated to allow the cells to reproduce.

Factor XIII for use within the present invention may be prepared from plasma according to known methods, such as those disclosed by Cooke and Holbrook (*Biochem. J.* 141: 799–84, 1974) and Curtis and Lorand (*Methods Enzymol.* 45: 177–191, 1976), incorporated herein by reference. The $a_2$ dimer form of factor XIII may be prepared from placenta as disclosed in U.S. Pat. Nos. 3,904,751; 3,931,399; 4,597,899 and 4,285,933, incorporated herein by reference. It is preferred, however, to use recombinant factor XIII so as to avoid the use of blood- or tissue-derived products that carry a risk of disease transmission and avoid contamination with other proteins.

Methods for preparing recombinant factor XIII are known in the art. See, for example, Davie et al., EP 268,772 and Grundmann et al., AU-A-69896/87, which are incorporated herein by reference in their entirety. Within a preferred embodiment, the factor XIII $a_2$ dimer is prepared cytoplasmically in the yeast *Saccharomyces cerevisiae*. The cells are harvested and lysed, and a cleared lysate is prepared. The lysate is fractionated by anion exchange chromatography at neutral to slightly alkaline pH using a column of derivatized agarose, such as DEAE FAST-FLOW SEPHAROSE™ (Pharmacia) or the like. Factor XIII is then precipitated from the column eluate by concentrating the eluate and adjusting the pH to 5.2–5.5, such as by diafiltration against ammonium succinate buffer. The precipitate is then dissolved and further purified using conventional chromatographic techniques, such as gel filtration and hydrophobic interaction chromatography.

Although it is preferred to use the factor XIII $a_2$ dimer within the present invention, other zymogen forms of factor XIII (e.g. $a_2b_2$ tetramer) may be used. Zymogen factor XIII is activated by thrombin present on the fibrin surface. However, activated factor XIII (factor XIIIa) may also be used.

Proteins for use within the present invention (including thrombin, plasmin, fibrinogen and factor XIII) can be obtained from a variety of mammalian sources, such as human, bovine, porcine and ovine. As will be appreciated by those skilled in the art, in prosthetic applications it is preferred to use proteins syngenesious with the patient in order to reduce the risk of inducing an immune response. Non-human proteins are particularly useful in the preparation of materials for veterinary use or for use in experimental models.

The following examples are offered by way of illustration, not limitation.

EXAMPLES

Reagents and Materials

For use in the experiments presented below, Hepes, Tris, and porcine heparin were obtained from Sigma Chemical Co., St. Louis, Mo.; D-phenylalanyl-L-prolyl-L-arginyl chloromethylketone (FPRCH$_2$Cl) from Calbiochem, San Diego, Calif.; the chromogenic substrate S-223 8 from Helena Laboratories, Mississauga, Ont., Canada; Na$^{125}$I from ICN Canada Ltd., Montreal, Canada; the Enzymobead reagent from Bio-Rad Laboratories, Mississauga, Ont. Canada; Na$_2$$^{51}$CrO$_4$ (200–500 Ci/g) from New England Nuclear, Dorval, Que., Canada; SP Sephadex, Sephadex G-25, DEAE-Cellulose, DEAE Sephadex, Sephacryl S-300 HR and Sepharose-lysine from Pharmacia Fine Chemicals, Piscataway, N.J. Polyethylene tubing (Intramedic PE 240, internal diameter 0.17 cm) was obtained from Clay-Adams, Parsippany, N.J. This tubing was rinsed with methanol and incubated overnight in Tris buffered saline (TBS, 0.1M NaCl, 0.05M Tris, pH 7.4) before it was exposed to protein solutions.

Human plasmin was obtained from Helena Laboratories, Beaumont, Tex.; bovine albumin from Boehringer Mannheim Canada, Dorval, Que, Canada; aprotinin from Mobay Chemical Co., New York, N.Y.; human α-thrombin was a generous gift of Dr. J. Fenton II, New York State Department of Health, Albany, N.Y.; apyras was prepared from potatoes as described previously (Kinlough-Rathbone et al., In: *Methods in Hematology, Measurements of Platelet Function* L. A. Harker et al., eds. Churchill Livingstone, Edinburgh, 1983; pp 64–91). Recombinant human platelet factor XIII (rFXIII) was provided by Zymogenetics, Seattle, Wash. The characteristics of this protein have been well-defined (Bishop et al., *Biochemistry.* 29, 1861–1869, 1990), and under reducing conditions it migrated as a single band on SDS-PAGE.

Human fibrinogen was purified from citrated human plasma by sequential β-alanine precipitation (Straughn et al. *Thrombos. Diathes. Haemorrh. (Stuttg)* 16: 198–206, 1966), and was 93–94% clottable. This fibrinogen was further purified to remove factor XIII, fibrin degradation products, and plasminogen using DEAE-cellulose chromatography according to the method of Lawrie et al. (*Biochem. Soc. Trans.* 7: 693–694, 1979).

Preparation of Fibrin Degradation Products

D-domain was prepared from purified human fibrinogen according to the method of Delvos et al. (*Haemostasis* 13: 99–105, 1988). Fibrinogen (100 mg in 5 mL TBS) was incubated with plasmin (15 casein units/mL) for 18 h at 37° C. in the presence of 2 mM CaCl$_2$. The reaction was terminated by the addition of aprotinin (100 KIU/mL), and the digest was passed over a Sepharose-lysine column. Haverkate et al. (*Thromb. Res.* 10: 803–812, 1977). The effluent was dialyzed against 10 mM sodium bicarbonate buffer (pH 8.9) and eluted from a DEAE-Sephadex column with a linear pH/salt gradient between the dialysis buffer and a 10 mM sodium bicarbonate buffer, pH 8.0, containing 0.3M NaCl. Samples from each of the protein-containing fractions were assessed by SDS-PAGE. Fractions with the highest purity of D-domain, verified as more than 90% pure by SDS-PAGE, were concentrated 10-fold using an ultrafiltration cell (Centriprep Concentrator, Areicon Division, W.R. Grace & Co., Danvers, Mass.) and stored at −70° C.

D-dimers were prepared from human fibrinogen (200 mg in 10 mL of TBS) incubated at 37° C. in the presence of rFXIII (5 µg/mL) and 30 U/mL human α-thrombin. Haverkate et al. (*Eur. J. Clin. Invest.* 9: 253–255, 1979). The cross-linked fibrin clot was removed, squeezed with filter paper to remove entrapped liquid, frozen at 70° C., lyophilized, ground to a fine powder, and resuspended (approx. 10 mg/mL) in a buffer at pH 7.8 containing 0.15M NaCl, 0.05M Tris, 5 mM CaCl$_2$, and 0.15 casein units/mL of plasmin. Brenner et al. (*J. Lab. Clin. Med.* 113: 682–688, 1989). After incubation at 37° C. for 18 h, aprotinin (100 KIY/mL) was added and the solution was chromatographed on Sepharose-lysine. D-dimer was isolated by passage of the effluent through a Sephacryl S-300 HR column eluted with TBS containing 0.028M sodium citrate, pH 7.4. The column had been calibrated with Bio-Rad gel filtration molecular weight standards. Fractions identified as containing D-dimer (195 kDa), verified as more than 90% pure by SDS-PAGE, were concentrated by ultrafiltration as described above and stored at −70° C.

Radiolabeling of Proteins

Fibrinogen, D-domain, and D-dimer were labeled with $^{125}$I using Enzymobeads according to the supplier's protocol. Enzymobeads and free iodide were removed by filtration through Sephadex G-25. Specific radioactivities were: fibrinogen 2×10$^5$ cpm/µg; D-domain 3.0×10$^6$ cpm/µg; D-dimer 1.0×10$^5$ cpm/µg. SDS-PAGE and autoradiography of the $^{125}$I-labeled fibrin and fibrin degradation products showed them to migrate as single bands that were coincident with their non-radioactive counterparts.

Preparation of Human Platelet: Red Blood Cell Suspensions

Blood was obtained from donors who, in the previous 2 weeks, had not received drugs that affect platelet function. Platelets were isolated, labeled with $^{51}$Cr(10 µCi/mL) in the first washing fluid, and resuspended in Tyrode-albumin solution which contained 2 mM $CaCl_2$, 1 mM $MgCl_2$, 0.14M NaCl, 2.7 mM KCl, 11.9 mM $NaHCO_3$, 0.42 mM $NaH_2PO_4$, 1 mg/mL glucose, 5 mM Hepes, 0.35% albumin, and 50 μL/mL apyrase (pH 7.35) (Kinlough-Rathbone et al., In: *Methods in Hematology, Measurements of Platelet Function* L. A. Harker et al., eds. Churchill Livingstone, Edinburgh, 1983; pp 64–91; Mustard et al., In: *Methods in Enzymology. Platelets: Receptors, Adhesion, Secretion.* Vol. 169. Part A., J. J. Hawiger, ed. Academic Press, New York, 1989, pp 3–11; Cazenave et al., *J. Lab. Clin. Med.* 93: 60–70, 1979). Red blood cells were isolated as described previously (Cazenave et al., *J. Lab. Clin. Med.* 93: 60–70, 1979) and added to the platelet suspension (40% hematocrit). The platelet count was adjusted to 500,000/μL.

EXAMPLE 1

Comparative Thrombogenecity of Fibrin Coating, and Factor XIII Cross-linked Fibrin Coating, of Polyethylene Tubing To assess the potential anti-thrombogenic effect of cross-linking of fibrin, polyethylene tubes were incubated in a labeled fibrinogen solution, either with or without the inclusion of 1 μg/mL of rFXIII in the solution. Segments of PE 240 tubing, 12 cm in length, were coated with thermally-denatured fibrinogen (Rubens et al., *J. Biomed. Mat. Res.* 26: 1651–1663, 1992) by filling them with a 1 mg/mL solution of fibrinogen, with or without 1 μg/mL of rFXIII, and heating the filled tube segments for 10 min. at 70° C. The segments were perfused with 40 mL of TBS and then filled with a 1 μg/mL solution of α-thrombin in 0.025M NaCl, 0.025M Tris, pH 7.4. After 5 min. at room temperature, the tubes were washed with 4 mL of this buffer and then perfused with 4 mL of TBS containing fibrinogen (1 mg/mL), $^{125}$I-fibrinogen (1 μg/mL), and 2 mM $CaCl_2$. After incubation for 5 min. at room temperature, the tubes were perfused with 40 mL of TBS and, unless indicated otherwise, were filled with 10 μM $FPRCH_2Cl$ in TBS and incubated for 5 min. to neutralize surface-bound thrombin. (Treatment with $FPRCH_2Cl$ was found to completely neutralize surface amidolytic activity as measured by the chromogenic substrate S-2238). The tubes were rinsed with 20 mL of TBS and platelet accumulation was measured immediately. Representative tubes (not perfused with the platelet: red blood cell suspension) were filled with 1× reducing sample buffer (Bio-Rad) and incubated at 37° C. for 24–48 h. This treatment removes protein from the PE surface. Aliquots of the solubilized tube contents, containing 20,000 cpm, were analyzed by SDS-PAGE.

To evaluate the comparative thrombogenicity attributable to the fibrin coating and cross-linked fibrin coating treatments, platelet accumulation on the differently treated tube segments was compared. The coated tube segments were attached to silicone tubing and assembled on a peristaltic pump (Drake-Willock, Model 4504, Portland, Oreg.). Suspensions of $^{51}$Cr-Labeled Platelets with unlabeled red blood cells at 37° C. were perfused through the tubing for 10 min. at 10 mL/min. and a wall shear rate of 764 $sec^{-1}$. The segments were then perfused under the same conditions for 10 min. with the modified Tyrode solution described above. The $^{51}$Cr remaining in the segments was measured using a Packard gamma counter. The number of platelets that accumulated per $mm^2$ was calculated from the surface area of the inside of the segments and the specific radioactivity of the platelets in the platelet: red blood cell suspension. Data from these studies were determined as a mean±standard deviation (S.D.), and were analyzed by Student's t-test (two-tailed).

The above studies showed that including rFXIII (1 μg/mL) in the solution of labeled fibrinogen did not diminish the amount of labeled fibrin on the PE tubing, and perfusion did not alter the amount of labeled fibrin on the surface. Analysis by SDS-PAGE of the surface of tubes coated with fibrin in the presence and absence of rFXIII showed the presence of an approximately 100 kDa band, corresponding to the γ—γdimer, in the fibrin formed in the presence of rFXIII, confirming that cross-linking had occurred. The inclusion of rFXIII (1 μg/mL) in the solution used to coat the tubing with labeled fibrin substantially decreased the extent of platelet accumulation from a value of 46,974±9702 platelets per $mm^2$ (no rFXIII) to 36,818±7964 platelets per $mm^2$ (with rFXIII) (n=12, p<0.01).

EXAMPLE 2

Comparative Thrombogenecity of D-Domain Coating, and Factor XIII Cross-linked D-Dimer Coating, of Polyethylene Tubing To assess the potential anti-thrombogenic effect of cross-linking of D-domain portions of fibrin, polyethylene tubes were incubated in a solution of either labeled fibrin D-domains or D-dimers, prepared as described above. Segments of PE 240 tubing, 12 cm in length, were filled with solutions of D-domain or D-dimer at 1 mg/mL in TBS, containing tracer amounts of the corresponding $^{125}$I-labeled fragment. The segments were incubated for 1 h at 23° C. and rinsed with a modified Tyrode solution (without $Ca^{2+}$ or $Mg^{2+}$, but containing 0.01M EDTA and 0.1% glucose). Platelet accumulation was measured as above. Briefly, the coated tube segments were attached to a peristaltic pump with silicone tubing, and suspensions of $^{51}$Cr-labeled Platelets with unlabeled red blood cells at 37° C. were perfused through the tubing for 10 min. at 10 mL/min. and a wall shear rate of 764 $sec^{-1}$. The segments were then perfused under the same conditions for 10 min. with the modified Tyrode solution described above. The $^{51}$Cr remaining in the segments was measured using a Packard gamma counter. The number of platelets that accumulated per $mm^2$ was calculated as above.

These studies showed that platelet accumulation on D-dimer coated polyethylene surfaces was greatly reduced compared to platelet accumulation on non cross-linked, D-domain coated surfaces. The surface protein concentration of the tubing coated with D-domain was 0.70±0.02 $μg/cm^2$, and the number of platelets that accumulated at high shear was 34,383±3905 per $mm^2$ (n=3). In contrast, the surface protein concentration of PE tubing coated with D-dimer was 0.13±0.05 $μg/cm^2$, and the number of platelets that accumulated was 563±257 per $mm^2$ (n=4). Thus, the thrombogenicity of the D-dimer coated surfaces measured 60-fold less than that of the D-domain coated surfaces. Even when these data are approximately normalized to account for the five-fold lower protein adsorption of the D-dimers to the tubing, compared to the protein adsorption of the D-domains, it is nonetheless evident that the D-dimer coating is at least ten times more anti-thrombogenic on polyethylene tubing than the D-domain coating.

Although certain embodiments of the invention have been described in detail for purposes of illustration, it will be readily apparent to those skilled in the art that the methods and products described herein may be modified without deviating from the spirit and scope of the invention. Accordingly, the invention is not limited by the above description but is to be determined in scope by the claims which follow.

We claim:

1. A method of coating a prosthetic surface with an anti-thrombogenic protein, comprising the step of:

contacting said prosthetic surface with a composition comprising multimers of fibrin degradation products, the multimers having cross-linked D-domains, to produce an anti-thrombogenic coating comprising said multimers on said prosthetic surface.

2. A method according to claim 1, wherein the composition consists essentially of said multimers of fibrin degradation products in a suitable carrier.

3. A method according to claim 1, wherein the composition consists of a solution of said multimers substantially free of intact fibrin and fibrin degradation products other than said multimers.

4. A method according to claim 1, wherein the composition is a solution and a concentration of said multimers in said solution is between approximately 0.1 mg/ml and 10 mg/ml.

5. A method according to claim 1, wherein the fibrin degradation products are plasmin cleavage products.

6. A method according to claim 1, wherein the composition is a solution and the prosthetic surface is incubated in the solution at a temperature of between approximately 20° C. and 25° C.

7. A method according to claim 1, wherein the composition is a solution and the prosthetic surface is incubated in the solution at a temperature of at least 56° C. but less than 100° C.

8. A method according to claim 1, wherein said multimers are formed by cross-linking intact fibrin with Factor XIII and subsequently generating the degradation products from said cross-linked intact fibrin by plasmin digestion.

9. A method according to claim 1, wherein the prosthetic surface is formed of a biologically compatible polymer.

10. A method according to claim 9, wherein the polymer is selected from the group consisting of polyethyleneterephthalate, polytetrafluoroethylene, expanded polytetrafluoroethylene, polymers of lactide-glycolide, polyglactin, polydioxanone, polyurethane, polypropylene and polyester.

11. A method according to claim 1, wherein the prosthetic surface is formed of a biomedically compatible material selected from the group consisting of stainless steel, titanium, cobalt chrome alloys and silicon-based materials.

12. A method according to claim 1, wherein the prosthetic surface is a surface of an artificial vascular implant.

13. A method according to claim 1, further comprising the step of seeding the prosthetic surface with endothelial cells.

14. A method according to claim 1, wherein the composition contains one or more additional proteins selected from the group consisting of basic fibroblast growth factor, endothelial cell growth factor, $\alpha 2$ macroglobulin, vitronectin, fibronectin, and cell-binding fragments of fibronectin.

15. A method according to claim 1, wherein the prosthetic surface is a surface of an artificial duct implant.

16. A method according to claim 15, wherein the artificial duct implant is selected from the group consisting of artificial urinary ducts, artificial kidney tubules, artificial lymphatic ducts, artificial bile ducts, artificial pancreatic ducts, indwelling catheters, shunts and drains.

17. A method according to claim 1, wherein the prosthetic surface is selected from the group consisting of a stent surface, an artificial urological implant surface, an artificial heart valve surface, an artificial internal organ surface, an artificial bone implant surface, a patch surface and a web surface.

18. A method according to claim 1, wherein the prosthetic surface is a surface of a heterograft or xenograft tissue or organ implant.

19. A prosthetic member comprising: a coated prosthetic surface prepared according to the process of claim 1.

20. A method of coating a prosthetic surface with an anti-thrombogenic protein, comprising the steps of:

contacting said prosthetic surface with a composition comprising multimeric fibrin degradation products in a suitable carrier, said multimeric fibrin degradation products having cross-linked D-domains and said composition being substantially free of intact fibrin and fibrin degradation products other than said multimeric fibrin degradation products, to produce an anti-thrombogenic coating consisting essentially of said multimeric fibrin degradation products on said prosthetic surface.

* * * * *